(12) United States Patent
Swindle

(10) Patent No.: US 8,188,344 B2
(45) Date of Patent: May 29, 2012

(54) COTTON VARIETY FM 9180B2F

(75) Inventor: Michael Swindle, Greenville, MS (US)

(73) Assignee: Bayer Cropscience AG, Monheim (DE)

( * ) Notice: Subject to any disclaimer, the term of this patent is extended or adjusted under 35 U.S.C. 154(b) by 284 days.

(21) Appl. No.: 12/420,351

(22) Filed: Apr. 8, 2009

(65) Prior Publication Data

US 2009/0255008 A1 Oct. 8, 2009

Related U.S. Application Data

(60) Provisional application No. 61/123,348, filed on Apr. 8, 2008, provisional application No. 61/195,602, filed on Oct. 8, 2008.

(51) Int. Cl.
*A01H 5/00* (2006.01)
*A01H 5/10* (2006.01)
*A01H 4/00* (2006.01)
*A01H 1/00* (2006.01)
*C12N 15/82* (2006.01)

(52) U.S. Cl. ........ 800/314; 800/260; 800/268; 800/276; 800/278; 800/279; 800/281; 800/265; 800/300; 800/302; 435/427

(58) Field of Classification Search .................. 800/260, 800/265, 270, 274, 276, 314, 268, 278, 279, 800/281, 300, 302; 435/410, 427
See application file for complete search history.

(56) References Cited

U.S. PATENT DOCUMENTS

| | | | |
|---|---|---|---|
| 6,008,438 A | 12/1999 | Keim | |
| 6,740,488 B2 | 5/2004 | Rangwala et al. | |
| 6,818,807 B2 | 11/2004 | Trolinder et al. | |
| 2004/0148666 A1 | 7/2004 | Rangwala et al. | |
| 2009/0049564 A1 | 2/2009 | Burdett | |

FOREIGN PATENT DOCUMENTS

| EP | 0 270 355 | 6/1988 |
|---|---|---|
| WO | WO 00/71733 | 11/2000 |

OTHER PUBLICATIONS

PVP 200100208 (Plant Variety Protection No. 200100208, May 29, 2001).*
Briggs, F.N. and Knowles, P.F., "Introduction to Plant Breeding," Chapters 11, 13 & 18, Reinhold Publishing Corporation, (1967).
Sakhanoko, H.F. et al., "Induction of Somatic Embryogenesis and Plant Regeneration in Select Georgia and Pee Dee Cotton Lines." Crop Science 44: 2199-2205 (2004).
Stam, P. "Marker-assisted Introgression: Speed at Any Cost?" Proceedings of the Eucarpia Meeting on Leafy Vegetable Genetics and Breeding, Noordwijkerhout, The Netherlands, Mar. 19-21, 2003. Eds. Th.J.L. van Hintum, A. Lebeda, D. Pink, J.W. Schut. p. 117-124 (2003).

* cited by examiner

*Primary Examiner* — David T Fox
*Assistant Examiner* — Keith Robinson
(74) *Attorney, Agent, or Firm* — Hunton Williams, LLP

(57) ABSTRACT

A novel cotton variety, designated as FM 9180B2F, is disclosed. The invention relates to seeds, plants, plant cells, plant tissue, harvested products and cotton lint as well as to hybrid cotton plants and seeds obtained by repeatedly crossing plants of variety FM 9180B2F with other plants. The invention also relates to plants and varieties produced by the method of essential derivation from plants of FM 9180B2F and to plants of FM 9180B2F reproduced by vegetative methods, including but not limited to tissue culture of regenerable cells or tissue from FM 9180B2F.

22 Claims, No Drawings

COTTON VARIETY FM 9180B2F

CROSS-REFERENCE TO RELATED APPLICATIONS

This application claims the benefit of U.S. Provisional Application No. 61/123,348 filed Apr. 8, 2008 and U.S. Provisional Application No. 61/195,602 filed Oct. 8, 2008, the disclosures of each of which are herein incorporated by reference in their entirety.

BACKGROUND OF THE INVENTION (i) Field of the Invention

This invention relates to the field of plant breeding. More particularly, the invention relates to a variety of cotton designated as FM 9180B2F, its essentially derived varieties and the hybrid varieties obtained by crossing FM 9180B2F as a parent line with plants of other varieties or parent lines.

(ii) Description of the Related Art

Cotton is an important, fiber producing crop. Due to the importance of cotton to the textile industry, cotton breeders are increasingly seeking to obtain healthy, good yielding crops of excellent quality.

Cotton is commonly reproduced by self-pollination and fertilization. This type of sexual reproduction facilitates the preservation of plant and variety characteristics during breeding and seed production. The preservation of these characteristics are often important to plant breeders for producing cotton plants having desired traits. Other methods of producing cotton plants having desired traits are also used and include methods such as genetic transformation via *Agrobacterium* infection or direct transfer by microparticle bombardment. Examples of such methods are disclosed, for example, in U.S. Pub. No. 20090049564, incorporated by reference herein in its entirety.

Due to the environment, the complexity of the structure of genes and location of a gene in the genome, among other factors, it is difficult to predict the phenotypic expression of a particular genotype. In additional, a plant breeder may only apply his skills on the phenotype and not, or in a very limited way, on the level of the genotype. As a result, a particular plant breeder cannot breed the same variety twice using the same parents and the same methodology. Thus, a newly bred variety is an unexpected result of the breeding process. Indeed, each variety contains a unique combination of characteristics.

By carefully choosing the breeding parents, the breeding and selection methods, the testing layout and testing locations, the breeder may breed at a particular variety type. In addition, a new variety may be tested in special comparative trials with other existing varieties in order to determine whether the new variety meets the required expectations.

SUMMARY OF THE INVENTION

The invention relates to seeds, plants, plant cells, parts of plants, cotton lint or fiber, and cotton textiles of cotton variety FM 9180B2F as well as to hybrid cotton plants and seeds obtained by repeatedly crossing plants of FM 9180B2F with other cotton plants. The invention encompasses plants and plant varieties produced by the method of derivation or essential derivation from plants of FM 9180B2F and to plants of FM 9180B2F reproduced by vegetative methods, including but not limited to regeneration of embryogenic cells or tissue of FM 9180B2F.

DETAILED DESCRIPTION OF THE INVENTION

The invention has been obtained by a general breeding process comprising the steps outlined below. (For reference, see chapter 11, "Breeding Self Pollinated Crops by Hybridization and Pedigree Selection," in Briggs and Knowles (1967).

Parent plants, which have been selected for good agronomic and fiber quality traits are manually crossed in different combinations. The resulting F1 (Filial generation 1) plants are self-fertilized and the resulting F2 generation plants, which show a large variability on account of optimal gene segregation, are planted in a selection field.

These F2 plants are observed during the growing season for health, growth vigor, plant type, plant structure, leaf type, stand ability, flowering, maturity, seed yield, boll type, boll distribution, boll size, fiber yield and fiber quality. Plants are then selected. The selected plants are harvested and the bolls analyzed for fiber characteristics and the seed cleaned and stored. This procedure is repeated in the following growing seasons, whereby the selection and testing units increase from individual plants in the F2, to multiple plant containing 'lines' (descending from one mother plant) in the F5 and the number of units decrease from approximately 2500 plants in the F2 to 20 lines in the F5 by selecting about 10-20% of the units in each selection cycle.

The increased size of the units, whereby more seed per unit is available, allows the selection and testing in replicated trials on more than one location with a different environment and a more extensive and accurate analyzing of the fiber quality.

The lines or candidate varieties become genotypically more homozygous and phenotypically more homogeneous by selecting similar plant types within a line and by discarding the so called off-types from the very variable F2 generation on to the final F7 or F8 generation.

Depending on the intermediate results the plant breeder may decide to vary on the procedure as described above such as by accelerating the process by testing a particular line earlier or retesting a line another year. He may also select plants for further crossing with existing parent plants or with other plants resulting from the current selection procedure.

By the method of recurrent backcrossing, as described by Briggs and Knowles supra, in chapter 13, "The Backcross Method of Breeding," the breeder may introduce a specific trait or traits into an existing valuable line or variety, while otherwise preserving the unique combination of characteristics of this line or variety. In this crossing method the valuable parent is recurrently used to cross it at least two or three times with each resulting backcross F1, followed by selection of the recurrent parent plant type, until the phenotype of the resulting F1 is similar or almost identical to the phenotype of the recurrent parent with the addition of the expression of the desired trait or traits.

This method of recurrent backcrossing eventually results in an essentially derived variety, which is predominantly derived from the recurrent parent or initial variety. This method can therefore also be used to get as close as possible to the genetic composition of an existing successful variety. Thus, compared to the recurrent parent the essentially derived variety retains a distinctive trait, which can be any phenotypic trait, with the intention to profit from the qualities of that successful initial variety.

Depending on the number of backcrosses and the efficacy of the selection of the recurrent parent plant type and genotype, which can be supported by the use of molecular markers as described by P. Stam, (2003), the genetic conformity with the initial variety of the resulting essentially derived variety may vary between 90% and 100%.

Other than recurrent backcrossing, as described herein, such essentially derived variety may also be obtained by the selection from an initial variety of an induced or natural occurring mutant plant, or of an occurring variant (off-type) plant, or of a somaclonal variant plant, or by genetic transformation of regenerable plant tissue or embryogenic cell cultures of the said initial variety by methods well known to those skilled in the art, such as Agrobacterium-mediated transformation as described by Sakhanokho et al., (2004), Reynaerts et al. (2000), Umbeck et al. (1988) and others. Examples of transgenic events transformed in this way are "LLCotton25," USDA-APHIS petition 02-042-01p (disclosing expression of a bar coding sequence from *Streptomyces hygroscopicus* encoding phosphinothricin-acetyl-transferase, operably linked to a cauliflower mosaic virus 35S promoter and 3' untranslated region from a nopaline synthase gene), "Cot 102," USDA-APHIS petition 03-155-01p (disclosing expression of the vip3A coding sequence from *Bacillus thuringiensis* encoding the VIP3A protein, operably linked to the *Arabidopsis thaliana* actin-2 promoter and the terminator from the *Agrobacterium tumefaciens* nopaline synthase gene), and "281-24-236," USDA-APHIS petition 03-036-01p (disclosing expression of the cry1F coding sequence from *Bacillus thurigiensis* encoding the Cry1F protein, operably linked to a synthetic promoter containing the *Agrobacterium tumefaciens* nopaline synthase promoter and four copies of the octopine synthase enhancer from *Agrobacterium tumefaciens* tumor inducing plasmid pTiAch5 and the bi-directional terminator ORF25 polyA) combined with "3006-210-23," USDA-APHIS petition 03-036-02p (disclosing expression of the cry1Ac coding sequence from *Bacillus thuringiensis* encoding the Cry1Ac protein, operably linked to the *Zea mays* ubiquitin 1 promoter and the bi-directional terminator ORF25 polyA). Information regarding these and other transgenic events referred to herein may be found at the U.S. Department of Agriculture's (USDA) Animal and Plant Health Inspection Service (APHIS) website. An "Event" is defined as a (artificial) genetic locus that, as a result of genetic engineering, carries a foreign DNA comprising at least one copy of the gene(s) of interest. Other methods of genetic transformation are well known in the art such as microprojectile bombardment. See, e.g., U.S. Publication No. 2009/0049564, which is incorporated by reference herein in its entirety.

The plants selected or transformed retain the unique combination of the characteristics of FM 9180B2F, except for the different expression of characteristics (e.g., one, two, three, four, or five characteristics) changed by the selection of the mutant or variant plant or by the addition of a desired trait via genetic transformation. Therefore, the product of essential derivation (i.e., an essentially derived variety) has the phenotypic characteristics of the initial variety, except for the characteristics that change as a result of the act of derivation. Plants of the essentially derived variety can be used to repeat the process of essential derivation. The result of this process is also a variety essentially derived from said initial variety.

In one embodiment, FM 9180B2F progeny plants are produced by crossing plants of FM 9180B2F with other, different or distinct cotton plants, and further selfing or crossing these progeny plants with other, distinct plants and subsequent selection of derived progeny plants. The process of crossing FM 9180B2F derived progeny plants with itself or other distinct cotton plants and the subsequent selection in the resulting progenies can be repeated up to 7 or 8 times in order to produce FM 9180B2F derived cotton plants.

FM 9180B2F has been obtained by introducing the Event MON 88913 (APHIS petition 04-086-01p) via a cross between a donor plant containing this Event and the cotton variety FM 958 (Plant Variety Protection Number 200100208), followed by two backcrosses of the F1 plants resulting from these crosses, that express the characteristics of FM 958 combined with the Event as described above, with plants of FM 958 resulting in the population F-BC2. The Events MON 531 (USDA-APHIS petition 94-308-01p) and MON 15985 (USDA-APHIS petition 00-342-01p) were introduced in FM 958 by crossing the donor plant containing these Events with the cotton variety FM 958, followed by two backcrosses of the F1 plants resulting from these crosses, that express the characteristics of FM 958 combined with the Events as described above, with plants of FM 958, resulting in the backcross population B2-BC2. The Events have been combined by crossing plants of F-BC2 with plants of B2-BC2 resulting in the FM 958 B2F BC3 population. After an additional cross of this population with the BCSI cotton line E0263, the variety FM 9180B2F has been selected.

FM 9180B2F is similar to the existing variety FM 958, but differs by its resistance to the insect pests Cotton Bollworm, Cotton Leafworm, Fall Armyworm, Pink Bollworm and Tobacco Budworm, as a result of the surprising expression of the Events MON 531 and MON 15985 in combination with the remainder of the characteristics of FM958 and the resistance to the herbicide glyfosate as a result of the surprising expression of the Event MON 88913 in combination with the remainder of the characteristics of FM 958.

Provided herein as embodiments of the invention are seeds, plants, plant cells and parts of plants of the cotton variety FM 9180B2F. Representative seeds of this variety will be deposited under rule 37 CFR 1.809, ATCC Accession No. PTA-12470. Plants produced by growing such seeds are provided herein as embodiments of the invention. Also provided herein are pollen or ovules of these plants, as well as a cell or tissue culture of regenerable cells from such plants. In another embodiment, the invention provides for a cotton plant regenerated from such cell or tissue culture, wherein the regenerated plant has the morphological and physiological characteristics of cotton cultivar FM 9180B2F, as described herein (e.g., Table 1), when grown in the same environmental conditions. In yet another embodiment, the invention provides methods of testing for a plant having the morphological and physiological characteristics of cotton cultivar FM 9180B2F. In one embodiment, the testing for a plant having the morphological and physiological characteristics of cotton cultivar FM 9180B2F is performed in the same field, under the same conditions and in the presence of plants of FM 9180B2F, e.g., plants grown from the seed deposited under ATCC Accession No. PTA-12470. In another embodiment, the characteristics to be tested for are those described herein (e.g., Table 1).

Another embodiment of the invention provides for a method of introducing a desired trait into cotton cultivar FM 9180B2F comprising: (a) crossing the FM 9180B2F plants, grown from seed deposited under ATCC Accession No. PTA-12470, with plants of another cotton line that comprise a desired trait to produce F1 progeny plants; (b) selecting F1 progeny plants that have the desired trait to produce selected F1 progeny plants; (c) crossing the selected F1 progeny plants with the FM 9180B2F plants to produce first backcross progeny plants; (d) selecting for first backcross progeny plants that have the desired trait and the physiological and morphological characteristics of cotton cultivar FM 9180B2F as described herein (e.g., Table 1), when grown in the same environmental conditions, to produce selected first backcross progeny plants; and (e) repeating steps (c) and (d) at least two times in succession to produce selected third or higher backcross progeny plants that comprise the desired trait and all of the physiological and morphological characteristics of cotton cultivar FM 9180B2F as described herein (e.g., Table 1), when grown in the same environmental conditions. Plants produced by this method have all of the physiological and morphological characteristics of FM 9180B2F, except for the characteristics derived from the desired trait.

Another embodiment of the invention provides for a method of producing an essentially derived plant of cotton variety FM 9180B2F comprising introducing a transgene conferring the desired trait into the plant. In another embodiment, the invention provides for a method of producing an essentially derived cotton plant from FM 9180B2F comprising genetically transforming a desired trait in regenerable cell or tissue culture from a plant produced by the invention, resulting in an essentially derived cotton plant that retains the expression of the phenotypic characteristics of cotton variety FM 9180B2F, except for the characteristics changed by the introduction of the desired trait.

Desired traits described herein include modified cotton fiber characteristics, herbicide resistance, insect resistance, bacterial disease resistance, fungal disease resistance, male sterility, modified carbohydrate metabolism and modified fatty acid metabolism. Such traits and genes conferring such traits are known in the art. See, e.g., US 20090049564, incorporated by reference herein in its entirety.

The invention also provides for methods wherein the desired trait is herbicide tolerance and the tolerance is linked to a herbicide such as glyphosate, glyfosinate, sulfonylurea, dicamba, phenoxy proprionic acid, cycloshexone, triazine, benzonitrile, bromoxynil and imidazalinone. The invention also provides for methods wherein the herbicide tolerance is an expression of the Event "LLCotton25" and the insect resistance is an expression of the Event "281-24-236", Event "3006-210-23" or a combination thereof, or Event "Cot 102."

Also included herein is a method of producing cotton seed, comprising the steps of using the plant grown from seed of cotton variety FM 9180B2F, of which a representative seed sample will be deposited under ATCC Accession No. PTA-12470, as a recurrent parent in crosses with other cotton plants different from FM 9180B2F, and harvesting the resultant cotton seed.

Another embodiment of this invention relates to seeds, plants, plant cells and parts of plants of cotton varieties that are essentially derived from FM 9180B2F, being essentially the same as this invention by expressing the unique combination of characteristics of FM 9180B2F, including the herbicide resistance of FM 9180B2F, except for the characteristics (e.g., one, two, three, four, or five characteristics) being different from the characteristics of FM 9180B2F as a result of the act of derivation.

Another embodiment of this invention is the reproduction of plants of FM 9180B2F by the method of tissue culture from any regenerable plant tissue obtained from plants of this invention. Plants reproduced by this method express the specific combination of characteristics of this invention and fall within its scope. During one of the steps of the reproduction process via tissue culture somaclonal, variant plants may occur. These plants can be selected as being distinct from this invention, but still fall within the scope of this invention as being essentially derived from this invention.

Another embodiment of this invention is the production of a hybrid variety comprising repeatedly crossing plants of FM 9180B2F with plants of a different variety or varieties or with plants of a non-released line or lines. In practice, three different types of hybrid varieties may be produced (e.g., Chapter 18, "Hybrid Varieties" in Briggs and Knowles, supra):

The "single cross hybrid" produced by two different lines, the "three way hybrid", produced by three different lines such that first the single hybrid is produced by using two out of the three lines followed by crossing this single hybrid with the third line, and the "four way hybrid" produced by four different lines such that first two single hybrids are produced using the lines two by two, followed by crossing the two single hybrids so produced.

Each single, three way or four way hybrid variety so produced and using FM 9180B2F as one of the parent lines contains an essential contribution of FM 9180B2F to the resulting hybrid variety and falls within the scope of this invention.

The invention also provides for cotton lint or fiber produced by the plants of the invention, reproduced from the invention, and plants essentially derived from the invention. The final textile produced from the unique fiber of FM 9180B2F also falls within the scope of this invention. The invention also provides for a method of producing a commodity plant product (e.g., lint, cotton seed oil) comprising obtaining a plant of the invention or a part thereof, and producing said commodity plant product therefrom.

The entire disclosure of each document cited herein (e.g., U.S. patent publications, non-patent literature, etc.) is hereby incorporated by reference.

Deposit Information

Applicant has deposited 2500 seeds of FM 9180B2F disclosed herein with the American Type Culture Collection (ATCC), 10801 University Boulevard, Manassas, Va 20110, USA, under ATCC Accession No. PTA-12470. The seeds were deposited with the ATCC on Jan. 30, 2012, under the Budapest Treaty..

EXAMPLE 1

Seeds were obtained from plants finally selected in the process of breeding the new variety "FM 9180B2F."

Seeds of the variety FM 9180B2F, of which a representative sample will be deposited, were planted, together with seeds of cotton variety FM 960B2R as reference variety, in field trials at two locations, as discussed hereunder.

The results as shown in Tables 1-4 were obtained from a pooled analysis of the data from these two trials.

1. BCS Research Station, Office location, Lubbock, Tex. 2006-2007. Conditions: trial was conducted in the field under irrigation with conventional management. Trial design for distinguishing characters: random complete block design with six replications and two 14 m row plots. For distinguishing characters: measurements were taken from 10 plants, from each of the 14 m plots.

2. BCS Research Clark location, Lubbock, Tex. 2006-2007. Conditions: trial was conducted in the field under irrigation with conventional management. Trial design for distinguishing characters: random complete block design with six replications and two 14 m row plots. For distinguishing characters: measurements were taken from 10 plants, from each of the 14 m plots.

Analysis of variance procedures were used to obtain least significant difference at the 5% level, using Agrobase software.

Tables 1-4 reflect the average expression of the characteristics of FM 9180B2F on these locations in 2006 and 2007. This expression can be different on other locations and/or in other years. The sample that will be deposited represents the variety and this sample can be analyzed for the expression of its phenotypic characteristics at any time and at any location.

FM 9180B2F is most similar and closely resembles FM 960B2R, but can be distinguished from its comparator variety FM 960B2R by the following: The herbicide event in FM 9180B2F (MON88913) has a broader window of application for glyphosate than the MON1445 event found in FM 960B2R; FM 9180B2F fruits lower (cm to 1st fruiting branch) than FM 960B2R; FM 9180B2F fruits nearly a node lower than FM 960B2R; FM 9180B2F has a lower mature plant height than FM 960B2R; FM 9180B2F has a lower lint percent and gin turnout than FM 960B2R; FM 9180B2F has a higher number of locules per boll than FM 960B2R.

TABLE 1

| Description of Characteristic | Possible Expression/Note | Variety FM 9180B2F | FM 960B2R |
|---|---|---|---|
| General Plant Type | | | |
| Plant Habit | spreading, intermediate, compact | Compact | Compact |
| Foliage | sparse, intermediate, dense | Intermediate | Intermediate |
| Stem Lodging | lodging, intermediate, erect | Erect | Erect |
| Fruiting Branch | clustered, short, normal | Normal | Normal |
| Growth | determinate, intermediate, indeterminate | Intermediate | Intermediate |
| Leaf color | greenish yellow, light green, medium green, dark green | Medium Green | Medium Green |
| Boll Shape | Length < Width, L = W, L > W | Length > Width | Length > Width |
| Boll Breadth | broadest at base, broadest at middle | Base | Base |
| Maturity | date of 50% open bolls | Early | Early |
| Plant | | | |
| cm. to first Fruiting Branch | from cotyledonary node | 19 | 23 |
| No. of nodes to 1st Fruiting Branch | excluding cotyledonary node | 7 | 7.8 |
| Mature Plant Height in cm. | cotyledonary node to terminal | 55 | 60 |
| Leaf: upper most, fully expanded leaf | | | |
| Type | normal, sub-okra, okra, super-okra | Normal | Normal |
| Pubescense | absent, sparse, medium, dense | Medium | Medium |
| Nectaries | present, absent | Present | Present |
| Stem Pubescense | glabrous, intermediate, hairy | Intermediate | Intermediate |
| Glands (Gossypol) | absent, sparse, normal, more than normal | | |
| Leaf | | Normal | Normal |
| Stem | | Normal | Normal |
| Calyx lobe | (normal is absent) | Normal | Normal |
| Flower | | | |
| Petals | cream, yellow | 100% Cream | 100% Cream |
| Pollen | cream, yellow | 100% Cream | 100% Cream |
| Petal Spot | present, absent | Absent | Absent |
| Seed | | | |
| Seed Index | g/100 seed fuzzy basis | 11.1 | 11.3 |
| Lint Index | g lint/100 seeds | | |
| Boll | | | |
| Lint percent, picked | | 40.6 | 41 |
| Gin Turnout, stripped | | 29.4 | 30.7 |
| Number of Seeds per Boll | | | |
| Grams Seed Cotton per Boll | | | |
| Number of Locules per Boll | | 4.5 | 4.2 |
| Boll Type | storm proof, storm resistant, open | Storm Resistant | Storm Resistant |
| Fiber Properties Method HVI | | | |
| Length, inches, 2.5% SL | | 1.18 | 1.19 |
| Uniformity (%) | | 81.8 | 81.2 |
| Strength, T1 (g/tex) | | 29.9 | 29.8 |
| Elongation, E1 (%) | | 5.6 | 4.5 |
| Micronaire | | 4.2 | 4.1 |
| Diseases, Insects and Pests | | | |
| Bacterial Blight race 1 | susceptible = S, moderately | | |
| Bacterial Blight race 2 | susceptible = MS | | |
| Bacterial Blight Race 18 | moderately resistant = MR, resistant = R | | |
| Verticillium Wilt | | | |
| Bollworm | | | |
| Cotton Leafworm | | | |
| Fall Armyworm | | | |
| Pink Bollworm | | | |
| Tobacco Budworm | | | |

TABLE 2

PLANT MEASUREMENT ANALYSIS

| ENTRY_NAME | LOCKS_BOLL (number) | SEED_INDEX (grams) | CMFB (cm) | NFB (cm) | HT (cm) |
|---|---|---|---|---|---|
| FM 9180B2F | 4.5 | 11.1 | 19.0 | 7.0 | 55.0 |
| FM 960B2R | 4.2 | 11.3 | 23.0 | 7.8 | 60.0 |

TABLE 3

YIELD DATA ACROSS ALL LOCATIONS

| | | | | LBS LINT/ACRE | | | | | |
|---|---|---|---|---|---|---|---|---|---|
| ENTRY NAME | MEAN % LINT | GIN TURNOUT | MEAN LOCS | PATSCHKE | SIDES | GAINES | INADALE | MELCHER | TULIA |
| FM 9180B2F | 40.6 | 29.4 | 1115 | 646 | 1517 | 1625 | 865 | 1028 | 1007 |
| FM 960B2R | 41.0 | 30.7 | 1208 | 693 | 1619 | 1735 | 950 | 1199 | 1053 |
| P > T* | 0.242 | 0.000 | 0.001 | | | | | | |

*Probability associated with a Student's paired t-Test, with a two-tailed distribution (0.196016)

TABLE 4

FIBER AND VISUAL DATA ACROSS ALL LOCATIONS

| | | | | | MEAN HVI FIBER QUALITY | | | | |
|---|---|---|---|---|---|---|---|---|---|
| ENTRY NAME | PLANT_HT (in) | STORM RESISTANCE | VISUAL RATING | MATURITY VISUAL | LEN (in) | UNIF (%) | STREN (g/tex) | ELONG (%) | MIC |
| FM 9180B2F | 33.8 | 5.3 | 7.0 | 47.3 | 1.18 | 81.8 | 29.90 | 5.6 | 4.2 |
| FM 960B2R | 37.0 | 4.3 | 7.5 | 45.3 | 1.19 | 81.2 | 29.8 | 4.5 | 4.1 |
| P > T* | 0.016 | 0.064 | 0.098 | 0.320 | 0.585 | 0.368 | 0.3210 | 0.001 | 0.394 |

*Probability associated with a Student's paired t-Test, with a two-tailed distribution (0.196016)

EXAMPLE 2

A variety that has been essentially derived from FM 9180B2F by the process of the transgression of the Event LLCotton 25, USDA-APHIS petition 02-042-01p, U.S. Pat. No. 6,818,807, into plants of the variety FM 9180B2F via the method of recurrent backcrossing and selecting the plants which express the characteristics of FM 9180B2F combined with the resistance to the herbicide glyfosinate.

EXAMPLE 3

A variety that has been essentially derived from FM 9180B2F by the process of the transgression of the Event LLCotton 25 via genetic engineering in regenerable cells or tissue of FM 9180B2F and the subsequent selection of regenerated plants, which express the characteristics of FM 9180B2F combined with the resistance to the herbicide glyfosinate.

EXAMPLE 4

A variety that has been essentially derived from FM 9180B2F by the selection of an induced or natural occurring mutant plant or off-type plant from plants of FM 9180B2F, which plant retains the expression of the phenotypic characteristics of FM 9180B2F and differs only from FM 9180B2F in the expression of one, or two, or three, or four, or five of the characteristics as listed in Table 1 and when grown side by side with FM 9180B2F on one or two locations in one or two growing seasons.

CITED REFERENCES

Lawrence P. Burdett, "Cotton Variety 02T15," U.S. Pub. No. 2009/0049564.

F. N. Briggs and P. F Knowles, "Introduction to Plant Breeding," Rheinhold Publishing Corporation, (1967).

H. F. Sakhanoko et al., "Induction of Somatic Embryogenesis and Plant Regeneration in Select Georgia and Pee Dee Cotton Lines," Crop Science 44: 2199-2205 (2004).

Umbecke et al., "Genetic Engineering of Cotton Plants and Lines," Published patent Application Number EP0290355 (1988).

Reynaerts, et al. "Improved method for *Agrobacterium* mediated transformation of cotton," Patent application number WO 0071733 (2000).

P. Stam, "Marker-assisted Introgression: Speed At Any Cost?" Proceedings of the Eucarpia Meeting on Leafy Vegetable Genetics and Breeding, Noordwijkerhout, The Netherlands, Eds. Th. J. L. van Hintum, A. Lebeda, D. Pink, J. W. Schut, pages 117-124 (19-21 Mar. 2003).

Trolinder, et al., "Herbicide tolerant cotton plants having event EE-GH1," U.S. Pat. No. 6,818,807 (2004).

What is claimed is:

1. A seed of cotton variety FM 9180B2F, wherein a representative seed of said variety has been deposited under ATCC Accession No. PTA-12470.

2. A plant, or part thereof, produced by growing the seed of claim 1.

3. The plant part of claim 2, wherein said plant part is pollen, an ovule or a cell.

4. A seed produced by the plant of claim 2.

5. A plant, or part thereof, obtained by vegetative reproduction from the plant or part thereof of claim 2, said plant or part thereof expressing all phenotypic characteristics of cotton variety FM 9180B2F.

6. A method of vegetative reproduction of cotton variety FM 9180B2F comprising culturing regenerable cells or tissue from FM 9180B2F.

7. A cell or tissue culture produced from the plant or part thereof of claim 2.

8. A cotton plant regenerated from the cell or tissue culture of claim 7, expressing all phenotypic characteristics of FM 9180B2F.

9. A method of producing F1 hybrid cotton seed, comprising crossing the plant of claim 2 with a cotton plant distinct from FM 9180B2F, and harvesting the resultant F1 hybrid cotton seed.

10. A F1 hybrid cotton seed produced by the method of claim 9.

11. A F1 hybrid cotton plant, or part thereof, produced by growing the seed of claim 10.

12. A plant obtained by the vegative reproduction of the plant of claim 11, expressing all phenotypic characteristics of the plant of claim 11.

13. A method of producing F1 cotton seed comprising crossing the plant of claim 11 with a cotton plant distinct from the plant of claim 11, and harvesting the resultant F1 hybrid cotton seed.

14. A method of producing an essentially derived cotton plant from FM 9180B2F, comprising introducing a transgene conferring a desired trait into the plant of claim 2.

15. A method of producing essentially derived cotton plant from FM 9180B2F comprising backcrossing the plant of claim 2 at least two times to obtain an essentially derived cotton plant from FM 9180B2F, said essentially derived cotton plant retaining the expression of the phenotypic characteristics of FM 9180B2F, except for those characteristics changed by said backcrossing.

16. The method of claim 14, wherein the desired trait is modified cotton fiber characteristics, herbicide tolerance, insect resistance, bacterial disease resistance, fungal disease resistance, male sterility, modified carbohydrate metabolism or modified fatty acid metabolism.

17. The method of claim 14, wherein the desired trait is herbicide tolerance and the tolerance to glyphosate, glyfosinate, sulfonylurea, dicamba, phenoxy proprionic acid, cycloshexone, triazine, benzonitrile, bromoxynil or imidazalinone is conferred.

18. The method of claim 16, wherein
the herbicide tolerance is an expression of a bar coding sequence from *Streptomyces byproscopicus* encoding phosphinothricin-acetyl-transferase, operably linked to a cauliflower mosaic virus 35S promoter and 3' untranslated region from a nopaline synthase gene and
the insect resistance is an expression of
a) the cry1F coding sequence from *Bacillus thurigiensis* encoding the Cry1F protein, operably linked to a synthetic promoter containing the *Agrobacterium tumefaciens* mannopine synthase promoter and four copies of the octopine synthase enhancer from *Agrobacterium tumefaciens* tumor inducing plasmid pTiAch5 and the bi-directional terminator ORF25 polyA;
b) the cry1Ac coding sequence from *Bacillus thuringiensis* encoding the Cry1Ac protein, operably linked to the *Zea mays* ubiquitin 1 promoter and the bi-directional terminator ORF25 polyA;
c) a combination of a) and b); or
d) the vip3A coding sequence from *Bacillus thuringiensis* encoding the VIP3A protein, operably linked to the *Arabidopsis thaliana* actin-2 promoter and the terminator from the *Agrobacterium tumefaciens* nopaline synthase gene.

19. A method of producing essentially derived cotton plants, comprising
selecting a mutant or variant plant from the plant of claim 2;
producing a regenerable cell or tissue culture from the selected plant; and
genetically transforming a desired trait into the regenerable plant cell or plant tissue, resulting in an essentially derived cotton plant that retains the phenotypic characteristics of cotton variety FM 9180B2F, except for the characteristics changed by the selection of the mutant or variant plant and the characteristics changed by the introduction of the desired trait.

20. A plant, or part thereof, produced by the method of claim 14, which retains the phenotypic characteristics of cotton variety FM 9180B2F, including a herbicide resistance characteristic of the expression of the Event "MON88913", except for the characteristics changed by the introduction of the desired trait.

21. A method of producing a cotton plant derived from cotton variety FM 9180B2F, comprising
a) crossing the plant of claim 2 with another cotton plant distinct from the plant of claim 2;
b) growing the resulting F1 seed to obtain a F1 plant and crossing the F1 plant with itself or with another, distinct cotton plant to obtain progeny seed; and
c) growing the progeny seed of step b) to obtain a progeny plant and crossing the progeny plant with itself or with another, distinct cotton plant, thereby producing a FM 9180B2F derived cotton plant.

22. The method of claim 21, further comprising repeating step c) up to eight times.

* * * * *